US009302062B2

(12) United States Patent
Shikani et al.

(10) Patent No.: US 9,302,062 B2
(45) Date of Patent: Apr. 5, 2016

(54) ADJUSTABLE AND BIASED-OPEN UNIDIRECTIONAL SPEAKING VALVE

(71) Applicant: Shikani Medical, LLC, Forest Hill, MD (US)

(72) Inventors: Alan H Shikani, Baltimore, MD (US); Thomas Root, Beverly, MA (US)

(73) Assignee: SHIKANI MEDICAL, LLC, Forest Hill, MD (US)

( * ) Notice: Subject to any disclaimer, the term of this patent is extended or adjusted under 35 U.S.C. 154(b) by 375 days.

(21) Appl. No.: 13/903,602

(22) Filed: May 28, 2013

(65) Prior Publication Data

US 2014/0352691 A1    Dec. 4, 2014

(51) Int. Cl.
| A61M 16/04 | (2006.01) |
| A61M 16/00 | (2006.01) |
| A61M 16/10 | (2006.01) |
| A61M 16/08 | (2006.01) |

(52) U.S. Cl.
CPC ....... *A61M 16/0468* (2013.01); *A61M 16/0816* (2013.01); *A61M 16/1045* (2013.01); *A61M 16/047* (2013.01); *A61M 16/0497* (2013.01)

(58) Field of Classification Search
None
See application file for complete search history.

(56) References Cited

U.S. PATENT DOCUMENTS

| 3,066,674 | A | * | 12/1962 | Capra | A61M 16/0468 128/207.16 |
| 3,279,487 | A | * | 10/1966 | Elam | A61M 16/208 128/204.19 |
| 3,498,315 | A | * | 3/1970 | Hester | F16K 15/04 137/375 |
| 3,865,106 | A | * | 2/1975 | Palush | A61M 16/08 128/200.18 |
| 3,906,996 | A | * | 9/1975 | DePass | A61M 16/12 128/205.11 |
| 3,913,607 | A | * | 10/1975 | Price | A61M 16/12 128/205.11 |
| 3,924,637 | A | * | 12/1975 | Swanson | A61M 16/0468 128/207.16 |
| 3,952,335 | A | * | 4/1976 | Sorce | A61F 2/203 128/207.16 |
| 4,040,428 | A | * | 8/1977 | Clifford | A61M 16/0468 128/207.16 |
| 4,449,523 | A | * | 5/1984 | Szachowicz | A61F 2/20 128/200.26 |
| 4,538,607 | A | | 9/1985 | Saul | |
| 4,844,113 | A | * | 7/1989 | Jones | F16K 17/363 137/39 |

(Continued)

OTHER PUBLICATIONS

International Search Report for Corresponding International PCT Application No. PCT/US14/39160, Dated Dec. 24, 2015.

*Primary Examiner* — Tan-Uyen (Jackie) T Ho
*Assistant Examiner* — Joseph D Boecker
(74) *Attorney, Agent, or Firm* — Hauptman Ham, LLP

(57) ABSTRACT

A speaking valve for management of a patient's airway comprising a body rotatably and removably attachable to a tracheotomy tube, the body having a first end communicable with the tracheotomy tube and a second end distal from the first end, an offset opening formed in the second end, a ramp disposed within the body, a ball having a diameter disposed within the chamber, the ball being adapted to be guided up and down the ramp and able to partially close the opening in the second end of the body, and the body and hence the chamber therein, at the option and control of the patient, wherein the ball is adapted to move up and down the ramp opening and partially closing the opening in the second end of the body and, as selected, exhalation by the patient proceeds through the patient's upper respiratory system and facilitates speaking by the patient.

28 Claims, 20 Drawing Sheets

(56) References Cited

U.S. PATENT DOCUMENTS

| | | | | |
|---|---|---|---|---|
| 5,433,747 A * | 7/1995 | Grundei | A61F 2/203 | 128/207.15 |
| 5,505,198 A * | 4/1996 | Siebens | A61M 16/0468 | 128/207.16 |
| 5,624,374 A * | 4/1997 | Von Iderstein | A61F 2/0009 | 128/DIG. 25 |
| 5,751,007 A * | 5/1998 | Weaver | B01J 19/123 | 250/494.1 |
| 5,899,832 A * | 5/1999 | Hougen | A63B 23/18 | 128/200.24 |
| 6,189,534 B1 * | 2/2001 | Zowtiak | A61M 16/0468 | 128/207.14 |
| 6,718,969 B1 * | 4/2004 | Rubin | A61M 15/0086 | 128/200.14 |
| 7,134,434 B2 * | 11/2006 | Truitt | A61M 16/08 | 128/200.24 |
| 2003/0005931 A1 * | 1/2003 | D. Jaffre | A61M 16/08 | 128/204.18 |
| 2007/0095350 A1 * | 5/2007 | Darkin | A61M 16/06 | 128/206.24 |
| 2011/0290240 A1 * | 12/2011 | Meyer | A61M 11/06 | 128/200.14 |
| 2012/0097170 A1 * | 4/2012 | Dawson | A61M 16/0468 | 128/207.16 |
| 2012/0103342 A1 * | 5/2012 | Shikani | A61M 16/0468 | 128/207.16 |
| 2012/0239141 A1 * | 9/2012 | Palmaz | A61F 2/2421 | 623/2.2 |
| 2013/0184619 A1 * | 7/2013 | Von Hollen | A61M 16/00 | 601/46 |

* cited by examiner

ADJUSTABLE AND BIASED-OPEN UNIDIRECTIONAL SPEAKING VALVE

BACKGROUND

Tracheotomy is a surgical procedure frequently performed to relieve obstruction of airflow through the larynx and upper trachea. One of its main side effects is loss of essential breathing functions including warming and filtering of air, coughing, smelling, tasting, swallowing, and, more devastatingly, speaking. Voice production requires vibration of the vocal cords from a stream of air passing through the larynx. When a tracheotomy tube is present, exhaled air follows the path of least resistance, and exits through the tracheotomy tube rather than up towards the larynx, limiting vibratory movement of the vocal cords, and hence limiting perceptual speech. This creates a psychological hardship, as communication is critical to patients' overall medical care and social interactions This problem can be particularly disruptive in children, where a tracheotomy can actually impact the development of normal language skills In order to redirect the air toward the vocal cords, the patient may use a finger to occlude the tracheotomy tube. Finger occlusion however has several limitations: it requires manual dexterity (which some patients may lack); it also requires coordination of phonation with breathing (which some patients may be unable to perform); and it is unsanitary. The use of a tracheotomy speaking valve enables tracheotomy patients to speak without having to occlude the tracheotomy tube with their finger. Unidirectional speaking valves have a displaceable element that allows air to flow through the cannula and into the lungs during inspiration and prevent air from flowing through the cannula during expiration. Thus, during expiration, air flows through the patient's upper airways, such as the subglottic trachea, larynx, pharynx, mouth, and nasal passages. As a result, tracheotomized individuals using a unidirectional tracheotomy valve are able to communicate orally and maintain clear upper airway passages by coughing or expelling air through the upper airway passages.

There are a number of unidirectional (one-way) speaking valves that close 100% upon exhalation (also referred to as "no leak" design valves), redirecting air from the tracheostomy tube upward through the larynx, permitting phonation and improvement of swallowing and of secretions management. These are flapper-type speaking valves, whereby a diaphragm abuts the frontal opening of the valve. The valve opens upon inhalation and forms an uninterrupted a tight closed no-leak seal upon exhalation, hence completely stopping the air from exiting through the tracheostomy valve upon exhalation. Such one-way flapper valves include for example: the Passy-Muir tracheostomy & ventilator swallowing and speaking valve (PMV 005) available from Passy-Muir Inc, the Montgomery tracheostomy speaking valve (product code 221201) and TRACOE® PhonAssist speaking valve (product code 650-T), both available from Boston Medical Products; the Hood speaking valve (product code SPV-3015); and the Shiley Phonate® speaking valve (product designation SSVO) available from Nellcor Puritan-Bennett LLC. These valves are generally of a similar size and configuration and are designed to slide onto a standard 15 millimeter (mm) external (ventilator) end of a tracheostoma tube or cannula. Also, prior U.S. Pat. No. 8,051,856 Bare & Scherer, assigned to Passy-Muir, Inc U.S. Pat. No. 802,316 by Fulgham describe similar types of flapper unidirectional speaking valves having a "no leak" design. This listing is not intended to be a representation that a complete search of all relevant art has been made, or that no more pertinent art than that listed exists, or that the listed art is material to patentability. Nor should any such representation be inferred.

Another type of valve, which is different from flapper type valves, is a unidirectional tracheotomy speaking valve with an external cylindrical housing chamber, that contains a ball acting as the displaceable element. The ball moves back and forth during inspiration and expiration, and is limited from going beyond the housing chamber during inspiration by a pin or a wire that extends into the posterior opening of the chamber and intersects a path of travel of the ball, preventing it from entering the patient's airway. In this design, the housing chamber is external to the tracheotomy tube and coupled to the cannula of a tracheotomy tube. U.S. Pat. No. 6,588,428 by Shikani et al describes a similar design unidirectional speaking valve except the housing chamber is internal and an integral part of the inner cannula of the tracheotomy tube.

One common clinical observation to the above unidirectional speaking valves is that, because all the valves close 100% and allow no air leak upon exhalation, airflow is always redirected to the vocal cords at exhalation. Hence, while the tracheotomized patient can breathe in through the speaking valve, he/she never has the possibility to breath out through the valve if he/she wishes (for example, while the patient is at rest and does not wish or need to redirect the air upward through the vocal cords in order to speak). Consequently the patient is not able to use any of these speaking valves concurrently with a Humidity Moisture Exchanger (HME) to benefit from humidification and filtration. Another concern is that, in order for the tracheotomized patient who is on the ventilator and who wishes to use a unidirectional speaking valve, the tracheotomy tube cuff must be deflated in order for the air to go around the tube and up towards the vocal cords, otherwise not only will voicing be impossible, but there is also a risk of complete closure of the airway circuit, a potentially life-threatening situation. In order to address these concerns, a different type of valve is required to allow at least some degree (even if slight) of air leak upon exhalation.

One of the purposes of the present disclosure is to describe a novel unidirectional speaking valve and a method to allow redirecting air from the tracheostomy tube upward through the larynx, permitting phonation and improvement of swallowing and of secretions management, with some degree (even if slight) of air leak without 100% closure of the airway circuit.

For a variety of reasons, patients may find themselves in respiratory failure that necessitates a tracheotomy and ventilator support. These conditions may include progressive respiratory insufficiency due for example to muscular dystrophies, post-polio syndrome, amyotrophic lateral sclerosis (ALS or Lou Gehrig's disease), severe deformities of the chest wall or spine, such as kyphoscoliosis or thoracoplasty. Acute respiratory failure may also require tracheotomy and mechanical support, due for example to acute neurologic events, strokes, high spinal cord injury acute pulmonary infections, upper airway obstructive lesions, etc.

Communication for handicapped ventilator-dependent patients is a difficult problem both for the patient and the healthcare personnel. Tracheotomy diverts air away from the vocal cords and interferes with the production of normal speech. This may be addressed by using a one-way speaking valve, which redirects the air flow toward the larynx.

Currently, there are only two single unidirectional valves that are available for use with the ventilator: the Passy-Muir tracheostomy speaking valve and the Montgomery® Ventrach™ Speaking Valve. These two devices are flapper type valves, hence allow air to enter the lungs through the tracheostomy tube but close 100% upon exhalation.

As previously mentioned, a critically important point for using the Passy-Muir or the Montgomery® Ventrach™ tracheostomy speaking valve concurrently with a ventilator is that the tracheotomy cuff must be deflated (to redirect airflow upward toward the vocal cords), otherwise there is risk of a dangerous closed airway circuit.

While cuff deflation is a must, it does create conditions which make it fairly difficult to introduce the ventilator patient to a speaking valve for the first time. Even though tracheotomized patients are eager to speak, there is significant patient reluctance toward cuff deflation, and it hence requires quite a bit of preparation and counseling on behalf of the speech-language pathologist to ensure that both the patient and family feel comfortable with speaking valve use while on a ventilator. Introducing the valve begins with an initial goal of restoring airflow through cuff deflation trials. The duration of the trials depends on the patient's medical status as well as ventilator settings and tracheotomy size. One particular patient may tolerate full cuff deflation within a couple of sessions, and another patient may only tolerate partial deflation trials over a period of weeks. The patient's tolerance to cuff deflation is determined by any changes in heart rate, desaturation, CO2 levels and voicing. If there are no adverse changes with full cuff deflation, the speech-language pathologist generally can then move forward with a speaking valve trial. However, some patients, such as those who have significantly compromised pulmonary status, such as an upper-airway obstruction or a particularly large or specialized tracheostomy tube, may not tolerate cuff deflation and may not even be candidates for speaking valves.

If, by mistake, the nurse or the medical staff introduce the speaking valve in the circuit and forget to deflate the cuff while the patient is hooked to the ventilator, this will result in a closed airway circuit, whereby air is blown by the ventilator into the trachea but the patient is not be able to exhale, since the valve is sealed and there is also an airtight seal around the tracheostomy tube. This will cause a hazardous increase in trans-tracheal pressure, subsequent hypo-oxygenation, hypercapnea and potentially even cause death of the patient. As a matter of fact, several such close call situations have been observed over the last few years due to this particular error by nurses and medical staff, and even worse, an accidental death of a paraplegic tracheotomized patient on the ventilator was recently documented.

Other than deflating a cuffed tracheotomy tube, the treating physician may opt to use a cuffless tracheostomy tube, or even a fenestrated tracheotomy tube. The problem is that, because of their lung physiology, many ventilator dependent patients are unable to tolerate the significant air leak observed with fenestrated tracheotomy tubes, cuffless and/or uncuffed tracheostomy tubes. These patients will then miss out on the advantages of a speaking valve, and end up forgoing the option of speech. They will also miss out on other benefits of speaking valves, including reduced secretions, increased sense of smell, reduced aspiration, and increased amount of oxygen in the blood. The treating physician may opt to manipulate the ventilator settings in order to help overcome some of the air leak in uncuffed ventilated patients with a tracheostomy; for example, they can try prolonging the inspiratory time using PEEP (positive end-expiratory pressure). The use of a longer inspiratory time and higher PEEP are additive in their ability to improve speaking rate; however, there are many patients who are unable to tolerate ventilator setting manipulations due to their physiology.

The above clinical observations of problems encountered by tracheotomy patients on ventilators (including the necessity to deflate the cuff in order to introduce the ventilator patient to a speaking valve, difficulty tolerating cuff deflation, risk of human error of erroneously inflating the cuff and causing hazardous increase in trans-tracheal pressure and hypercapnea) prompted the present inventors to invent a new type of valve designed to solve, in at least some embodiments, the problem of "no leak" valves. This, a new type of valve, is unique in a sense that it does not close 100% upon exhalation.

DESCRIPTION OF THE DRAWINGS

One or more embodiments are illustrated by way of example, and not by limitation, in the figures of the accompanying drawings, wherein elements having the same reference numeral designations represent like elements throughout and wherein.

DETAILED DESCRIPTION

Figure 1:
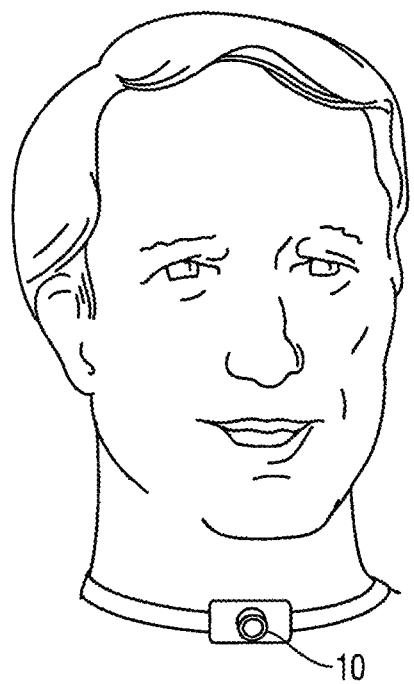
FIG. 1 is a diagram of a tracheotomy tube in a patient according to an embodiment.

FIG. 1 is a diagram of a tracheotomy tube 10 surgically implanted in the throat of a patient for airway management. A removably-mounted speech valve 12 (also referred to as a speaking valve) is mounted on the end of the tracheotomy tube extending outwardly from the patient's throat at an angle of approximately 20 degrees.

Figure 2:
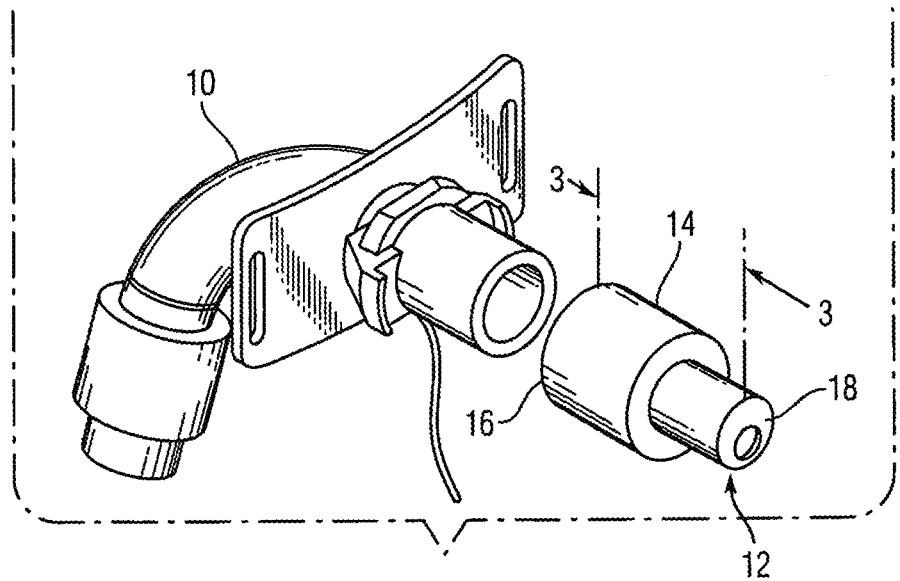
FIG. 2 is a detailed exploded parts view of a speaking valve according to an embodiment and a tracheotomy tube.

FIG. 2 is a detailed exploded parts view of speech valve 12 and tracheotomy tube 10. Speech valve 12 has a body 14 with a first end 16 for communication with the outer end of tracheotomy tube 10. The diameter of first end 16 of body 14 is larger than the diameter of a second end 18 of the body and forming a chamber having an internal step 20 within the body (as shown in FIG. 3).

Figure 3:
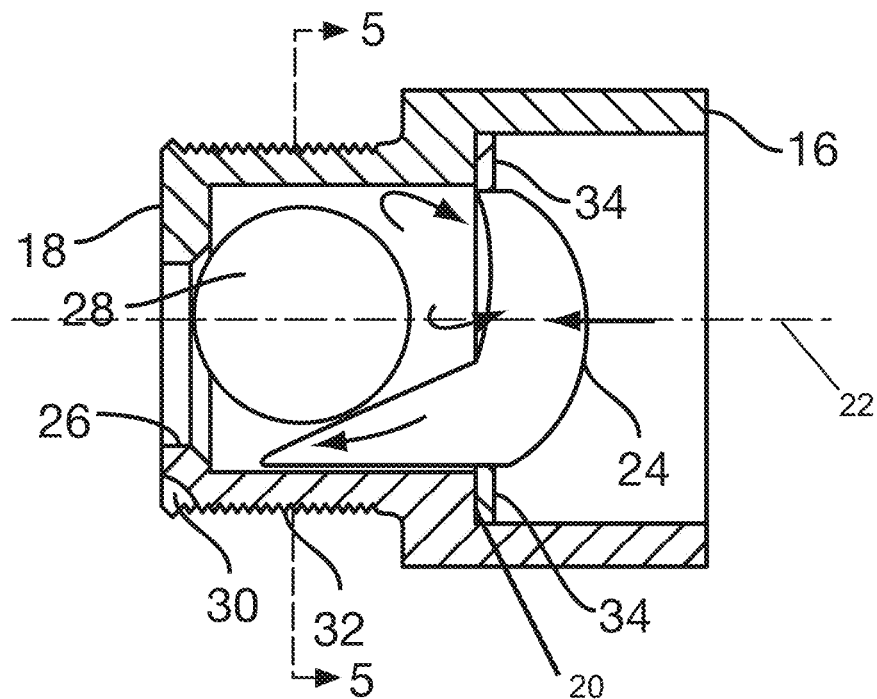
FIG. 3 is a cross-section taken along the lines 3-3 of FIG. 2 of the speaking valve in a down position.
Figure 5:
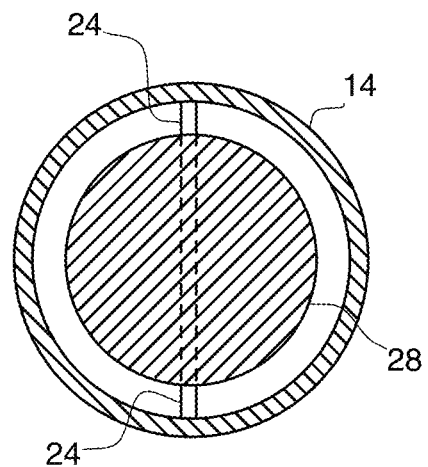
FIG. 5 is an axial cross-section of a speaking valve according to an embodiment.
Figure 6:
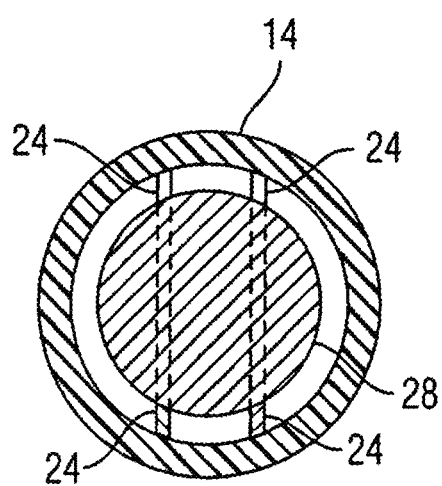
FIG. 6 is an axial cross-section of a speaking valve according to an embodiment.

FIG. 3 is a cross-section taken along the lines 3-3 of FIG. 2. First end 16 of body 14 is open. Second end 18 of body 14 has a frontal opening 26 formed therein which is offset from a central axis 22 of the body. Within body 14 is a ramp 24. A portion of ramp 24 slopes upwardly at an acute angle toward first end 16 of body 14. FIG. 5 is a cross-section view of body 14 showing ramp 24. FIG. 6 is a cross-section view of body 14 showing a pair of ramps 24, in accordance with an embodiment.

In at least some embodiments, body 14 includes a plurality of circumferentially spaced ramps 24. A portion of each ramp slopes upwardly at an acute angle toward first end 16 of body 14. In at least some embodiments, ramp 24 slopes upward at an angle other than an acute angle. In at least one embodiment, there are two parallel ramps 24, although more or fewer ramps may be used.

Within body 14, between frontal opening 26 and ramp 24, there is disposed a ball 28 for regulating airflow through valve 12. The ball has a diameter which is larger than the diameter of the frontal opening 26. Ramp 24 is positioned within body 14 to retain ball 28 within the body. In at least one embodiment, ramp 24 extends vertically and is positioned along a horizontal midline of body 14. Ramp 24 has a defined slope to hold the ball forward toward frontal opening 26.

In at least some embodiments having plural ramps, plural ramps are spaced apart from each other a distance which is less than the diameter of ball 28 to retain the ball within body 14. The plural ramps form a channel or guide to keep ball 28 along a midline axis, making movement of the ball less turbulent and more efficient. The plural ramps have a defined slope to hold the ball fully forward toward frontal opening 26.

Figure 4:
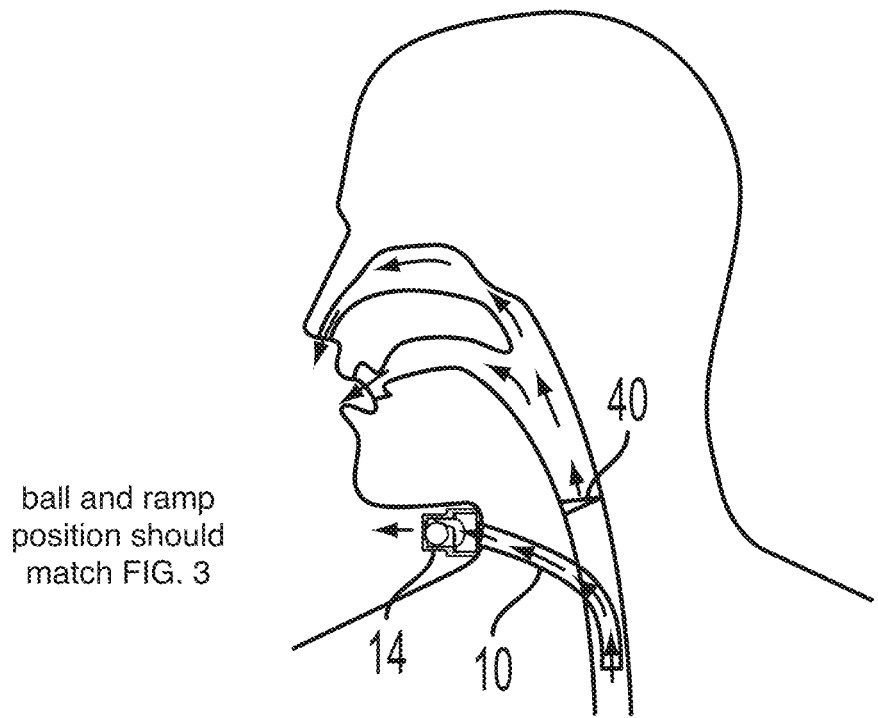
FIG. 4 is a cross-section view of a speaking valve according to an embodiment and connected to a tracheotomy tube in a patient.

In an "in rest" position, if body 14 is in a desired approximately horizontal position, ball 28 is automatically seated adjacent the frontal opening 26, thereby partially sealing the frontal opening if the patient is neither inhaling nor exhaling (FIGS. 3-5). The air passageway in the patient's upper airway is open for the passage of air and air passes over the vocal cords 40 enabling the patient to speak. At the same time, a lesser volume of air is able to pass around ball 28 and out frontal opening 26.

An indexing means 30 is formed on second end 18 of body 14 which is usable to determine the orientation of the body. Body 14 is rotatable with respect to tracheotomy tube 10 through 180 degrees by the patient (or the patient's caregiver) to provide an "up" and a "down" position of the body. In at least some embodiments, body 14 is rotatable through greater or lesser degrees by the patient. The outer surface of body 14 has threads 32 or ribs formed thereon to provide a better grip to rotate the body.

In at least one embodiment, indexing means 30 is a notch or non-round portion of the second end of body 14 located near frontal opening 26 in the body. In at least some other embodiments, indexing means 30 is a protrusion extending outwards from the second end of body 14. Other indexing means known to persons skilled in the art may be used to provide an indexing means that may be sensed tactilely by the patient.

Figure 7:
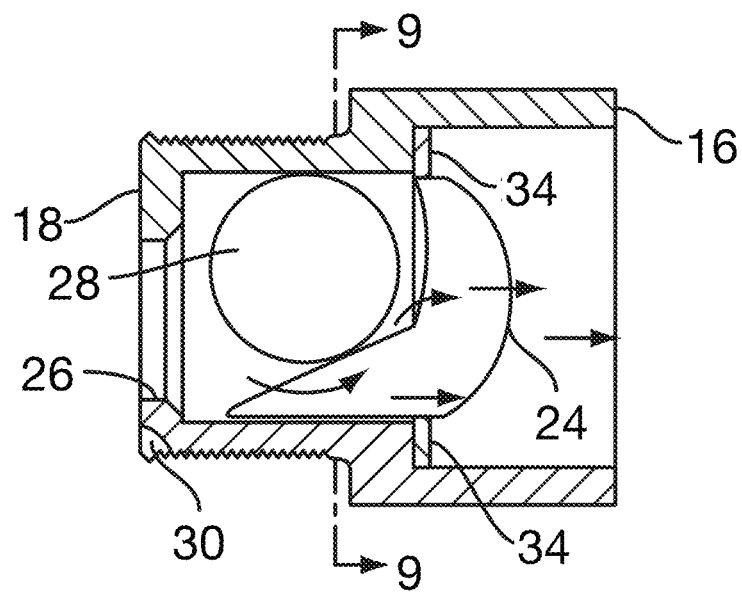
FIG. 7 is a cross-section taken along the lines 3-3 of FIG. 2 of the speaking valve in a down position.
Figure 8:
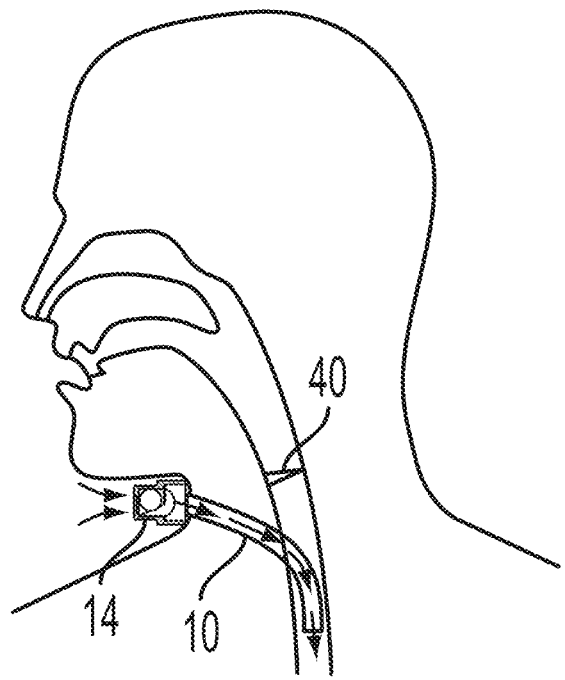
FIG. 8 is a cross-section view of a speaking valve according to an embodiment and connected to a tracheotomy tube in a patient.
Figure 9:
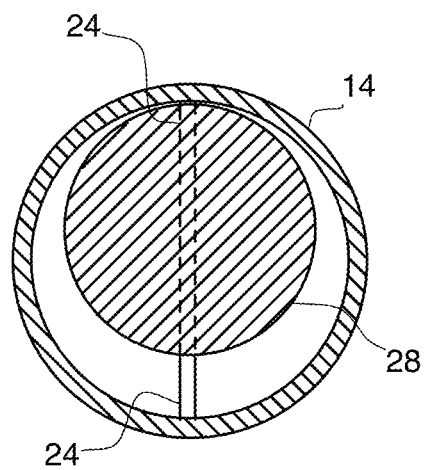
FIG. 9 is an axial cross-section of a speaking valve according to an embodiment.
Figure 10:
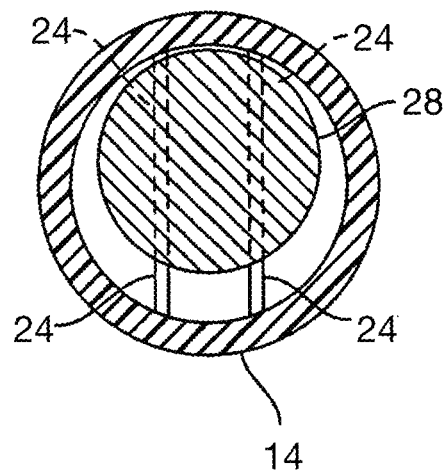
FIG. 10 is an axial cross-section of a speaking valve according to an embodiment.

As shown in FIGS. 7-9, if the indexing means is in the "down" position (i.e., indexing means 30 rotatably positioned at the bottom of body 14), and the patient inhales, the incoming air moves ball 28 up the ramp 24 toward the tracheotomy tube 10 and air flows around the ball, around the ramp and into the patient's lungs.

Figure 11:
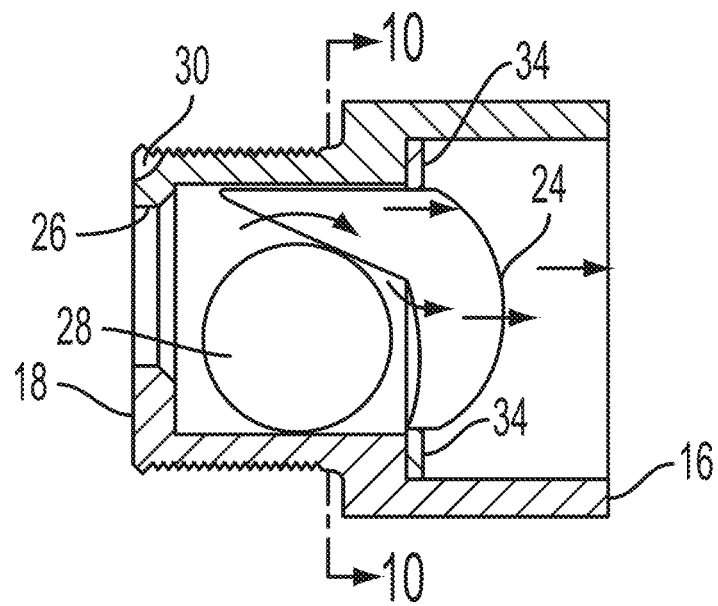
FIG. 11 is a cross-section taken along the lines 3-3 of FIG. 2 of the speaking valve in an up position.
Figure 12:
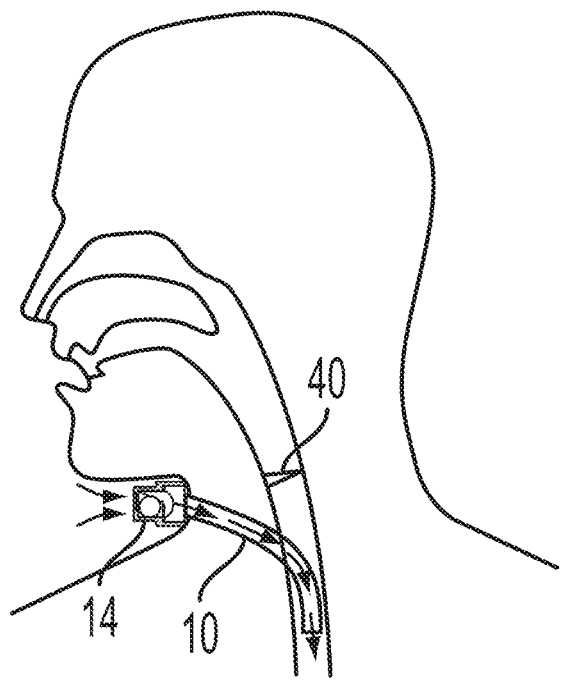
FIG. 12 is a cross-section view of a speaking valve according to an embodiment and connected to a tracheotomy tube in a patient.

If indexing means 30 is in the "up"/biased-open position (FIGS. 11-12), and the patient in the resting position, ball 28 rests posteriorly in the chamber toward the tracheotomy tube, allowing free flow of air. As the patient inhales, incoming air flows over the ball, around the ramp, and into the patient's lungs.

Figure 13:
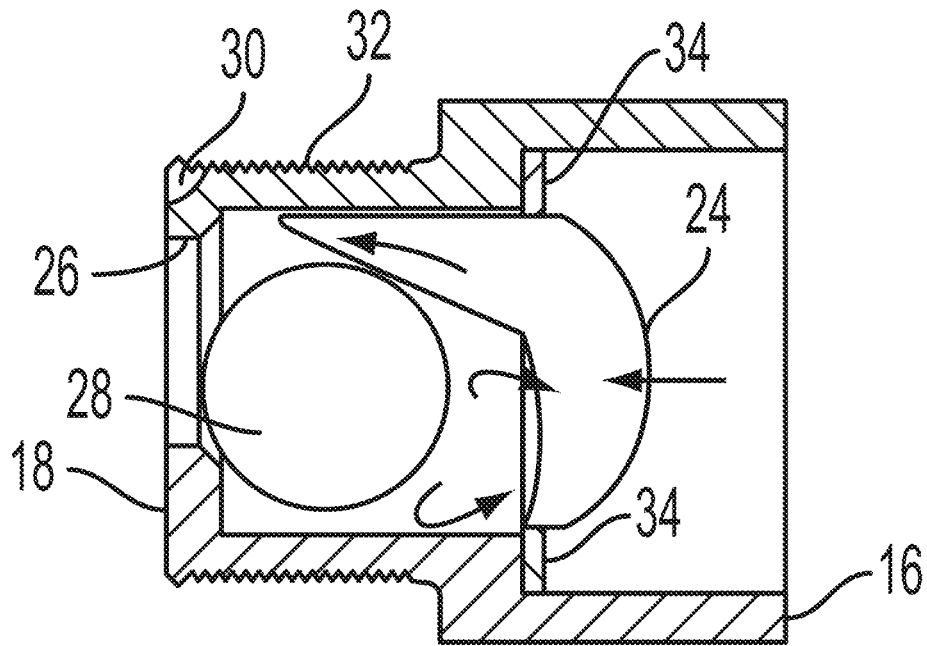
FIG. 13 is a cross-section taken along the lines 3-3 of FIG. 2 of the speaking valve in an up position.
Figure 14:
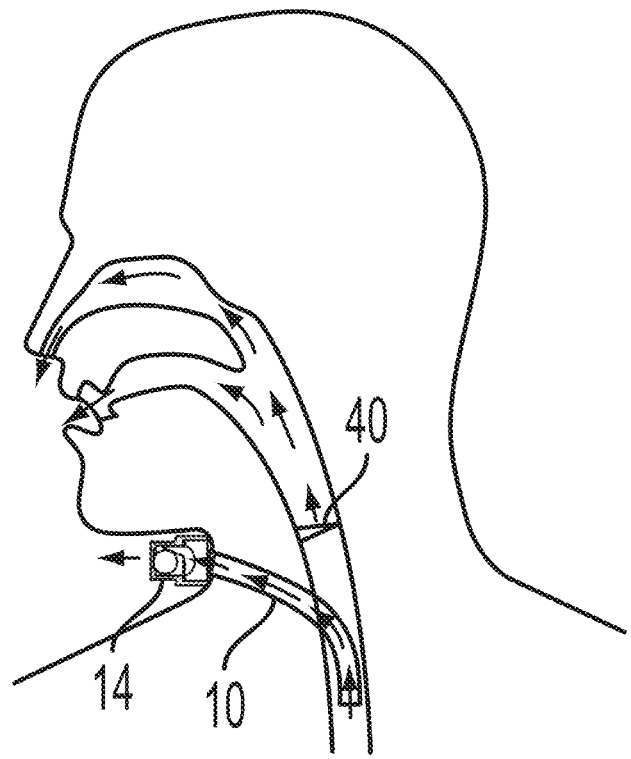
FIG. 14 is a cross-section view of a speaking valve according to an embodiment and connected to a tracheotomy tube in a patient.

If indexing means 30 is in the "up" position, when the patient exhales (FIGS. 13 and 14) ball 28 is displaced toward frontal opening 26 but the ball does not rise upwardly to the eccentrically formed frontal opening which is near the upper portion of body 14 when in the "up" position. No seal occurs in the frontal opening and air moves out of the patient's lungs, through the tracheotomy tube, and exits out of the valve.

However, with indexing means 30 in the "up" position, if the patient increases the exhalation force, the ball is forced upwardly in the chamber toward frontal opening 26 and the ball contacts ramp 24 and is prevented from fully seating in the frontal hole wherein a smaller volume of air flows through the valve and a larger volume of air is forced through the upper airway of the patient. In this scenario, the patient can speak since air is passing over the patient's vocal cords 40.

Thus, in at least one embodiment, the present disclosure describes a method of using the speaking valve in two different positions ("up" or "down"), and providing a positive ball positioning feature depending on how the housing chamber is rotated, hence greatly improving performance.

In the "down" mode, ball 28 is automatically directed forward and held in position toward but not fully seated in front opening 26 of the valve body 14, when the patient is breathing regularly at rest. This innovation allows the ball to sit inside frontal opening 26 and provide a leaky or non-fully seated seal to the valve with no expiratory air required to seat the ball in the opening ("biased-closed position").

In the "up" mode, ball 28 has a tendency to sit away from frontal opening 26, closer to the posterior opening of the chamber, providing a more open airflow passage ("biased-open position") hence allowing the patient to breathe easier. Additionally, ball 28 now requires a conscious effort in terms of exhalation force, to position the ball toward the frontal opening and partially seal off airflow. Because of this, exhaled air exits through the valve and is partially redirected through the patient's upper airway. Alternately, the patient is able to force the ball to partially seal when re-direction of airflow is desired for speech production. Ramp 24 is connected to a ring 34 which is disposed against the internal step 20 such that ramp 24 extends inwardly into the chamber in body 14. Ring 34 is keyed and ultrasonically welded to the step of the body to retain the ramp in place and in a proper orientation. The keying mechanism may be a tab formed on the ring with a cooperating notch formed in the step, or the tab may be formed on the step and the notch may be formed on the ramp's ring. Other keying mechanisms known to persons skilled in the art are usable.

In an alternate mode, the valve including the body, the ramp and the ball, is mounted within the cannula of the tracheotomy tube. Although the valve cannot be rotated, the valve operates in a manner as described above.

Having the exhaled air from the patient make contact with heat moisture exchange (HME) media is essential to the function of an HME filter. Because HME filters function only when air from the patient is exhaled across the media, and then returned to the patient, use of an HME filter is not possible with all other current unidirectional speaking valves which do not allow two-way airflow (air in and air out).

Prior to the valve design of the present disclosure, patients had to choose either to wear a speaking valve for communication and forgo the benefit of an HME filter, or alternatively to wear an HME filter and forgo the benefits of wearing a speaking valve. In the present disclosure, a cap containing fibers for HME is removably attached to the second end of the body. The novel ball valve's guiding design is unique in a sense that when the indexing means is in the "up" position (biased-open), the ball rests posteriorly inside the chamber, greatly facilitating airflow. This position accommodates the use of an HME filter as follows.

Upon normal and soft regular inhalation and exhalation, and with the valve in the "up" position (biased-open), air is uniquely allowed to flow back in and out through the valve (because the valve does not close 100% upon exhalation), and through the HME filter, making contact with the filter media. In this way, the patient receives the benefit of the HME filtered air upon inspiration. However, with the valve in this same position, the patient is also able to choose to have the ball nearly close frontal opening 26 at will, allowing redirection of a significant (although not all) of the exhaled air over the vocal cords, in order to produce speech. No repositioning of the valve itself is necessary. This is accomplished simply by providing increased expiratory effort and/or volume in order to drive the ball forward and vertically up the frontal wall, and toward the frontal opening to partially seat the ball and partially seal off airflow. The process of redirecting a significant volume of the exhaled air over the vocal cords is even more efficient with the valve in the "down" position (biased-closed), as the valve naturally rolls down the ramp and the patient does not need to provide increased expiratory effort and/or volume to move the ball forward toward the frontal opening.

One or more embodiments of the speaking valve uniquely allow the tracheotimized patient to realize the benefits of both automatic speech and humidification concurrently.

Obviously, many modifications may be made without departing from the basic spirit of the present invention. Accordingly, it will be appreciated by those skilled in the art that within the scope of the appended claims, the invention may be practiced other than has been specifically described herein.

According to an embodiment of the present disclosure, a biased-open speaking valve is provided for assisting phonation in a wearer of a tracheostomy tube who is not on the ventilator and another aspect of the present disclosure for a wearer of a tracheotomy tube who is on the ventilator. Both aspects are about how to redesign the ball unidirectional speaking valve so that, to allow some degree of airflow leak (hence avoiding 100% upon exhalation), and at the same time allow enough airflow redirection upwards towards the vocal cords to allow speech.

One or more embodiments of the present disclosure describe a novel valve and method for assisting phonation in a wearer of a tracheostomy tube who is not on the ventilator: The valve consists of an external cylindrical housing chamber that contains a ball acting as the displaceable element. The ball moves back and forth during inspiration and expiration, and is limited proximally (tracheal side) from going beyond the housing chamber during inspiration by a ring and at least one circumferentially-spaced ramp disposed within the body of the chamber. The valve has a frontal opening which is eccentric (off-center) formed in the second end offset from a central axis of the chamber. If the speaking valve is in "valve up" (bias-open) position, the ball is forced to travel "up" the ramp, which hinders, to a certain degree, the ability of the ball to immediately seat in the frontal opening. Further hindrance against the closure of the frontal opening upon exhalation is provided by small circular indentation that is added to the frontal opening.

One of the novelties in the speaking valve hence includes:

A body with an internal ramp at a predetermined angle (anywhere from 0.01 to 50 degree angle) that forces the ball to ride up the ramp when the valve is in the "valve up" position, and hence have the ability to interfere with the sealing of the frontal opening and with the amount of exhaled air redirected through the laryngeal opening.

A body with an internal block at 6 O'clock (6 O'clock corresponds to the "valve up" position) which interferes with upward movement of the ball, and hence interfere with the sealing of the frontal opening and with the amount of exhaled air redirected through the laryngeal opening.

One or more small indentation(s), bump(s), or dimples at the eccentric frontal opening that interferes with the complete sealing of the ball into the frontal opening of the speaking valve and allows some escape of air through the opening, both when the valve is in the "valve up" position or when the valve is in the "valve down" position, and hence interferes with the amount of exhaled air redirected through the laryngeal opening.

Small fenestrations/holes in the body of the valve which allow a certain degree of air leak and hence interfere with 100% airtight seal of the body of the valve, both when the valve is in the "valve up" position or when the valve is in the "valve down" position. The degree of leak may be made variable by rotating a ring around the area of the fenestrations, and hence occluding the ring to a variable and quantifiable degree.

If placed in the "bias-open" position ("valve up"), the novel valve hereby described incorporates different possible features that are all original, and that either interfere with movement of the ball (hence preventing the complete closure of the frontal opening during the exhalation process) and/or allow some escape of air through the frontal opening up exhalation (again preventing the complete closure of the frontal opening during the exhalation process). This is a novel feature that none of the flapper valves has, as they are designed to be always 100% closed at exhalation.

Figure 15:
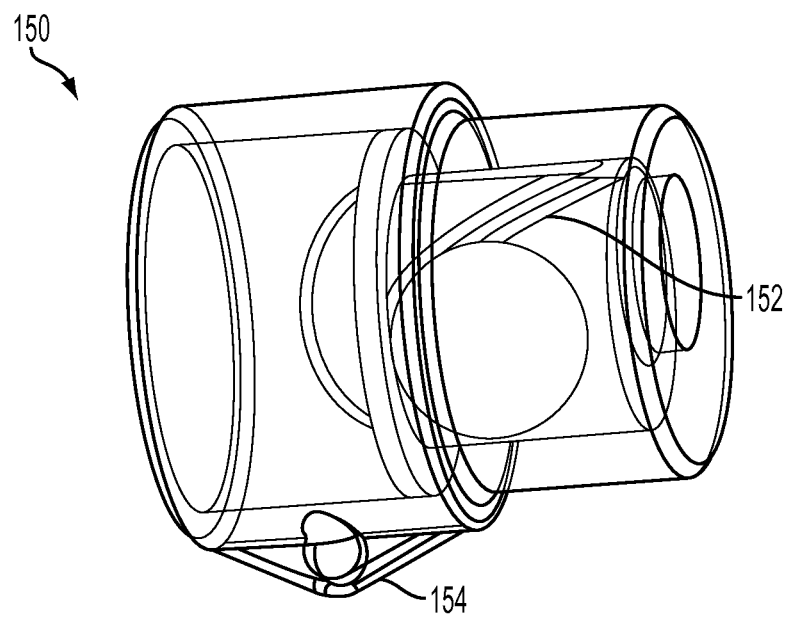
FIG. 15 is a perspective view of a speaking valve according to an embodiment in an up position.

FIG. 15 is a perspective view of a speaking valve 150 according to another embodiment. The walls of speaking valve 150 are shown transparent for ease of viewing the interior mechanism. Speaking valve 150 is similar in operation and functionality to speaking valve 12. Speaking valve 150 differs from speaking valve 12 in at least two aspects. Speaking valve 150 comprises a pair of curvilinear-sloped circumferentially-spaced ramps 152 in place of single ramp 24. Also, speaking valve 150 comprises an indexing mechanism 154 in place of indexing mechanism 30.

Figure 16:
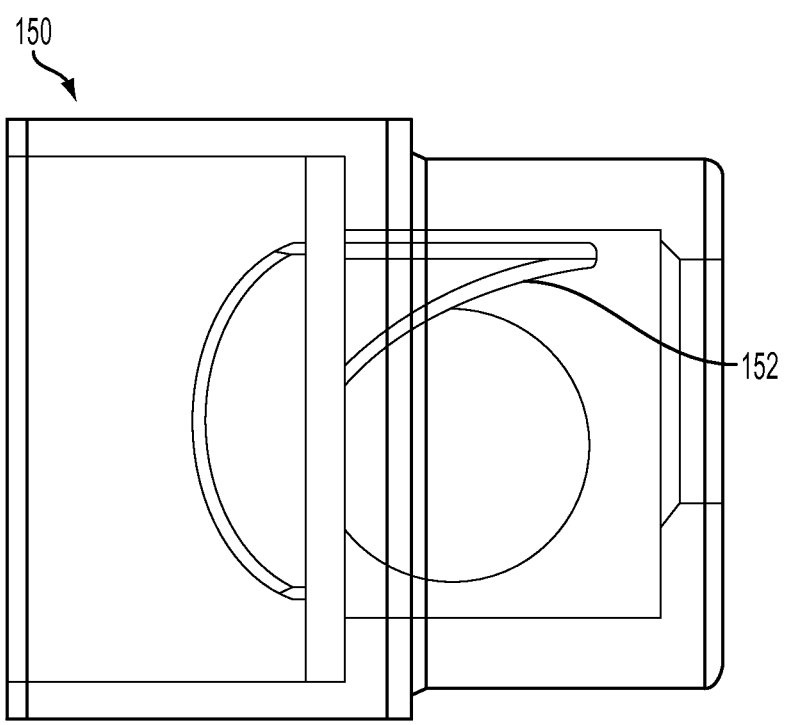
FIG. 16 is a side view of the speaking valve of FIG. 15.

FIG. 16 is a side view of the FIG. 15 embodiment.

Figure 17:
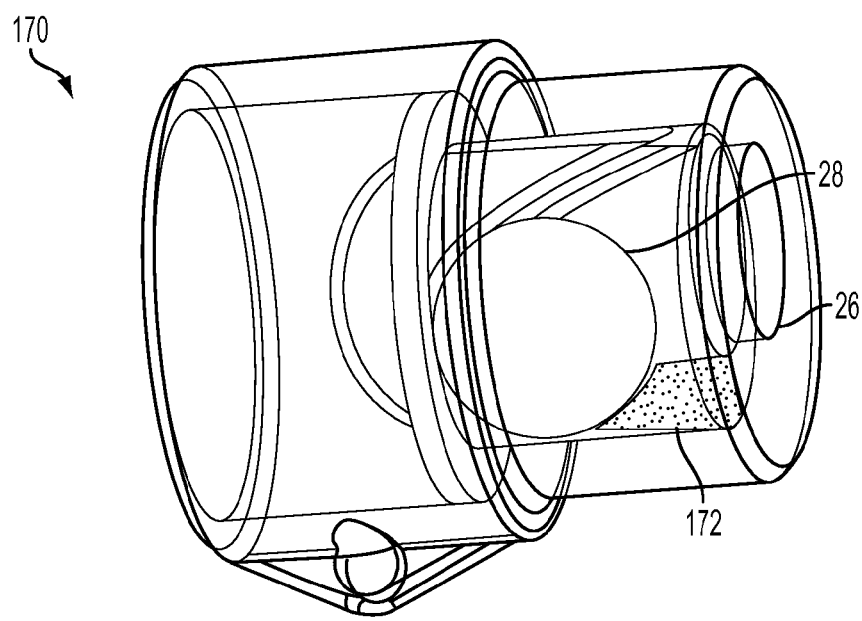
FIG. 17 is a perspective view of a speaking valve according to an embodiment in an up position.

FIG. 17 is a perspective view of a speaking valve 170 according to another embodiment in an up position. The walls of speaking valve 170 are shown transparent for ease of viewing the interior mechanism. Speaking valve 170 is similar in operation and functionality to speaking valve 150. Speaking valve 170 differs from speaking valve 150 in comprising a blocking ramp 172 positioned at a lower front corner adjacent frontal opening 26. Blocking ramp 172 is positioned in body 14 opposite the extension of ramp 24. Blocking ramp 172 comprises an upward sloping portion with the valve in an upward or biased-open position. If valve 172 is in an upward position, ramp 24 is on the upper surface of the interior of the valve and blocking ramp 172 is on an opposite lower surface of the interior. With blocking ramp 172 in this position, an additional exhalation effort is used to force ball 28 into position against the blocking ramp and partially sealing frontal opening 26. Blocking ramp 172 further prevents the ability of ball 28 to move into position to seal frontal opening 26. In at least some embodiments, blocking ramp 172 comprises a single ramp. In at least some embodiments, blocking ramp 172 comprises a plurality of circumferentially-spaced ramps. In at least some embodiments, the angle of ramp 24, given the addition of blocking ramp 172, need not be acute.

Figure 18:
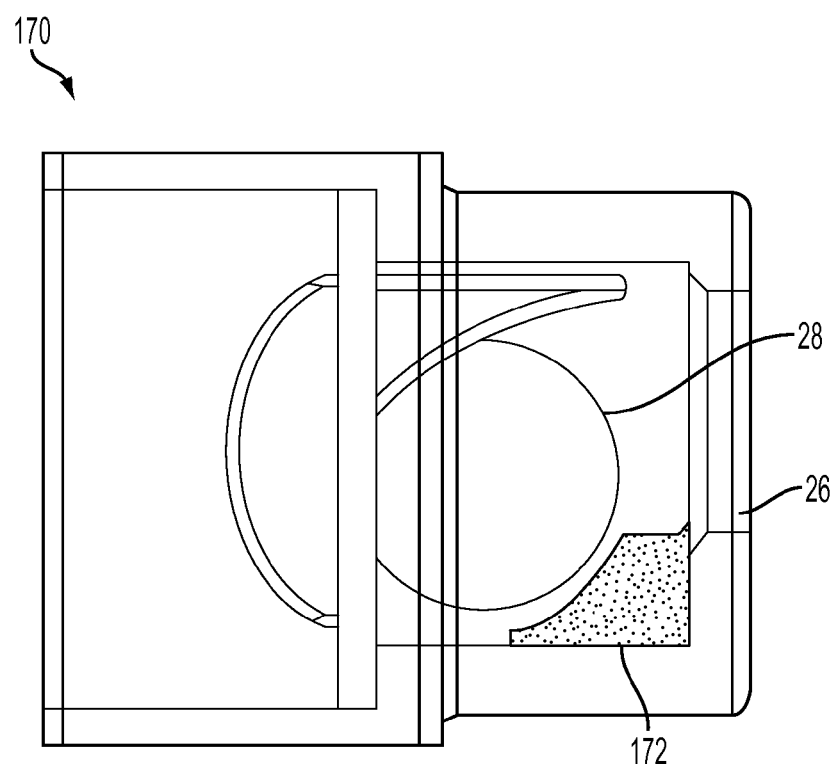
FIG. 18 is a side view of the speaking valve of FIG. 17.

FIG. 18 is a side view of the speaking valve 170 of FIG. 17.

Figure 19:
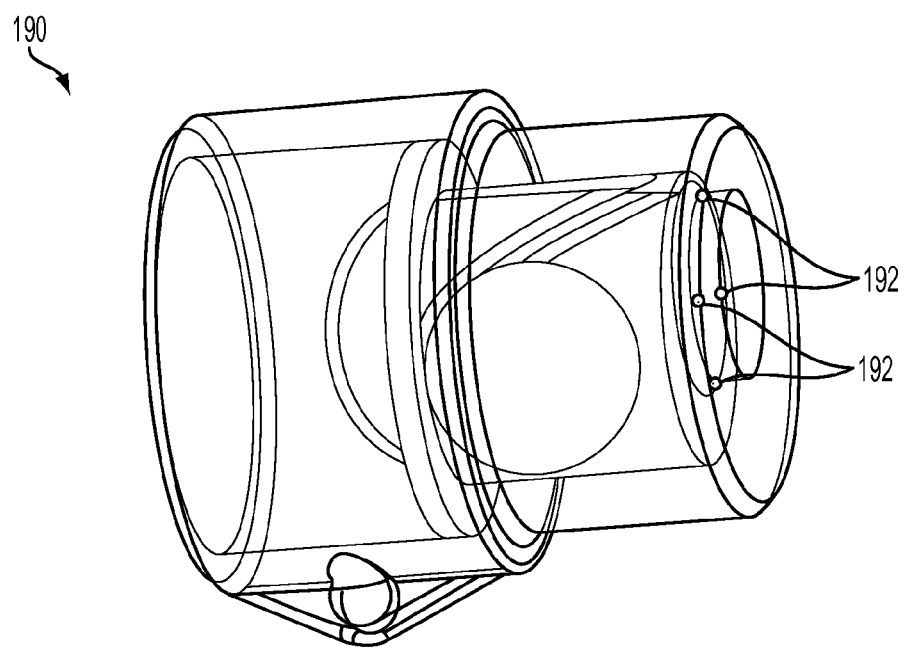
FIG. 19 is a perspective view of a speaking valve according to an embodiment in an up position.

FIG. 19 is a perspective view of a speaking valve 190 according to another embodiment in an up position. The walls of speaking valve 190 are shown transparent for ease of viewing the interior mechanism. Speaking valve 190 is similar in operation and functionality to speaking valve 150. Speaking valve 190 differs from speaking valve 150 in comprising a plurality of impediments 192 within body 14 and surrounding frontal opening 26. The impediments 192 comprise at least one indentation, bump, or dimple. The impediments 192 prevent ball 28 from completely sealing against frontal opening 26. Valve 190 comprises four (4) circumferentially spaced impediments 192 surrounding and adjacent frontal opening 26. In at least some embodiments, valve 190 comprises greater or lesser number of impediments 192. In at least some embodiments, impediments 192 are non-equidistantly spaced from each other. In at least some embodiments, the impediments 192 are sized to prevent sealing of ball 28 against frontal opening 26. In at least some embodiments, impediments 192 provide sufficient interference to prevent complete closure of frontal opening 26 that there is no need for interference provided by ramp 24. In at least some embodiments having impediments, ramp 24 has an angle other than an acute angle.

Figure 20:
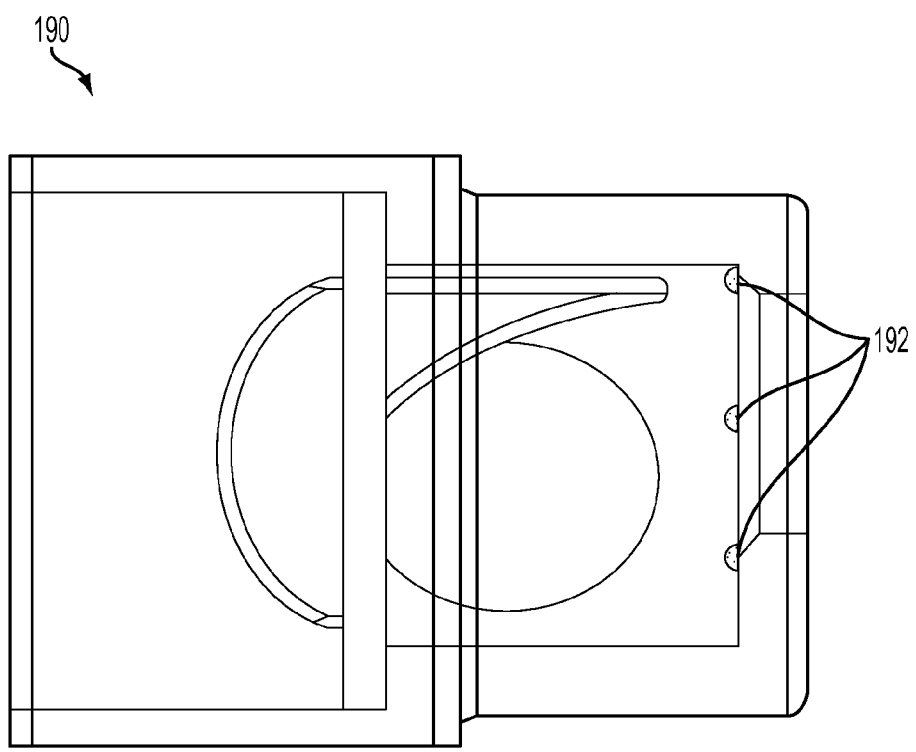
FIG. 20 is a side view of the speaking valve of FIG. 19.

FIG. 20 is a side view of the speaking valve 190 of FIG. 19.

Figure 21:
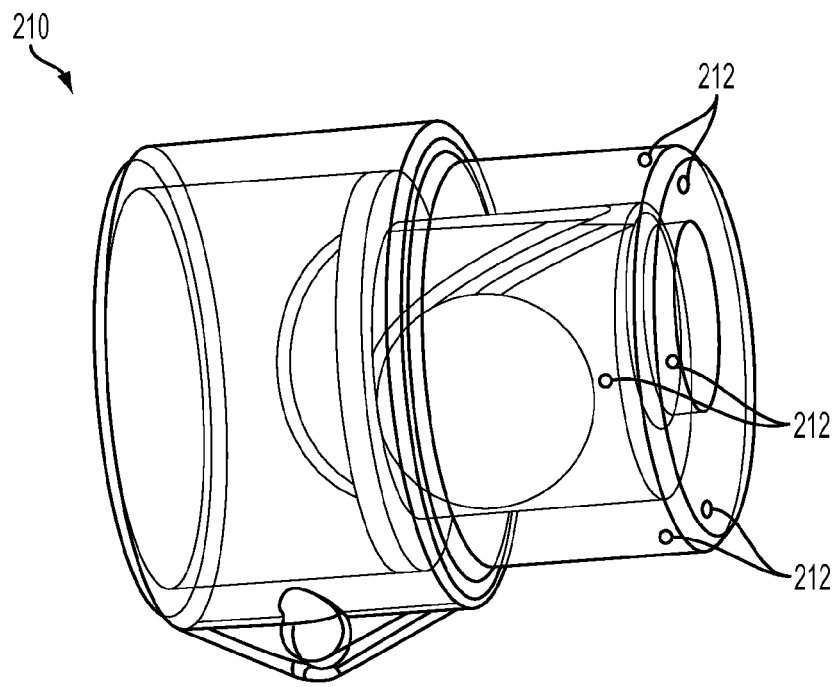
FIG. 21 is a perspective view of a speaking valve according to an embodiment in an up position.

FIG. 21 is a perspective view of a speaking valve 210 according to another embodiment in an up position. The walls of speaking valve 210 are shown transparent for ease of viewing the interior mechanism. Speaking valve 210 is similar in operation and functionality to speaking valve 150. Speaking valve 210 differs from speaking valve 150 in comprising a plurality of openings 212 (also referred to as holes or fenestrations) formed through body 14 and surrounding frontal opening 26. Bumps 212 prevent ball 28 from completely sealing against frontal opening 26. Valve 210 comprises six (6) circumferentially spaced openings 212 surrounding and adjacent frontal opening 26. In at least some embodiments, openings 212 are solely formed in second end 18 of valve 210. In at least some embodiments, openings 192 are solely formed in body 14 adjacent second end 18. In at least some embodiments, valve 210 comprises greater or lesser number of openings 212. In at least some embodiments, openings 212 are non-equidistantly spaced from each other. In at least some embodiments, the size of openings 212 is greater or lesser to allow greater or lesser amount of air flow.

Figure 22:
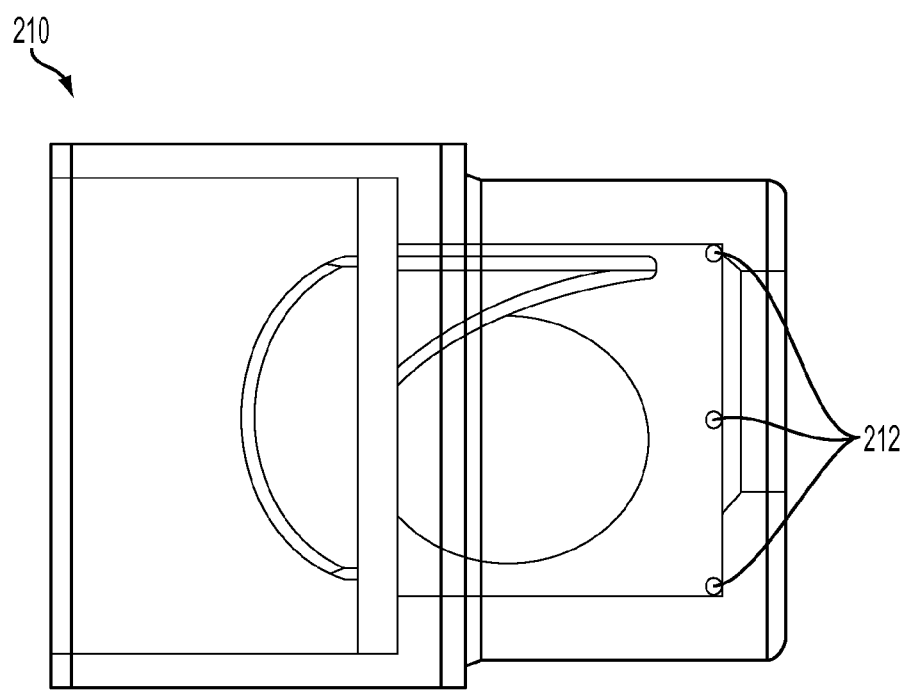
FIG. 22 is a side view of the speaking valve of FIG. 21.

FIG. 22 is a side view of the speaking valve of FIG. 21.

Another novelty of the present speaking valve is that because it allows airflow passage during exhalation, the "bias open" valve lets the patient couple a Humidity Moisture Exchange (HME) filter directly to the speaking valve, where it will fit over the new housing chamber like a cap. This enables the patient to breathe through the valve, in and out, to warm and humidify the breathed air, and concurrently speak when he/she wishes by giving a slightly stronger exhalation. As air flows out of the lungs through the tracheotomy/speaking valve/HME filter combined unit, the natural body temperature and humidity from the lung warms and humidifies the foam inside the HME. None of the previously described unidirectional speaking valves allow this new feature as they all close 100% at exhalation and do not allow any air leak.

Because HME filters function only when air from the patient is exhaled across the HME media, and then returned to the patient, use of an HME filter is not possible with any of the flapper unidirectional speaking valves. Prior to the ball valve design, patients had to choose either to wear a speaking valve for communication and forgo the benefit of an HME filter, or alternatively to wear an HME filter and forgo the benefits of wearing a speaking valve. The novel ball valve's guiding design is unique in a sense that when the housing is in the "valve up" ("bias-open") position, the speaking valve is hindered from 100% seal (either by a ramp that slopes upwardly at an acute angle toward, or by bumps or fenestrations), and upon normal exhalation, air is allowed to flow in and out through the valve and the HME filter (when attached). However, with the valve in this same position, the patient can also choose to allow redirection of some of the exhaled air over the vocal cords, in order to produce speech.

Figure 23:
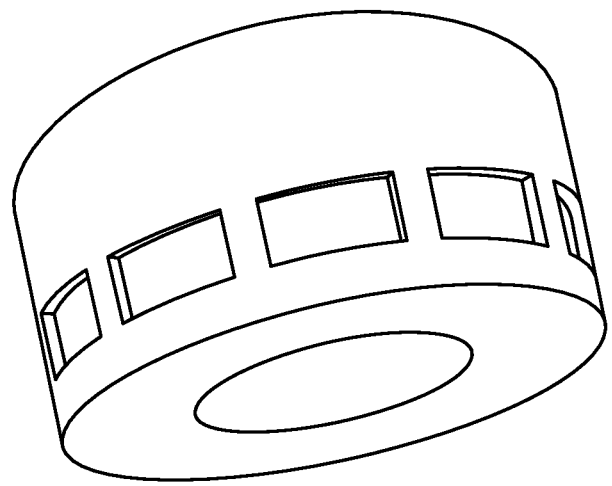
FIG. 23 is a perspective view of a heat moisture exchange filter according to an embodiment.
Figure 24:
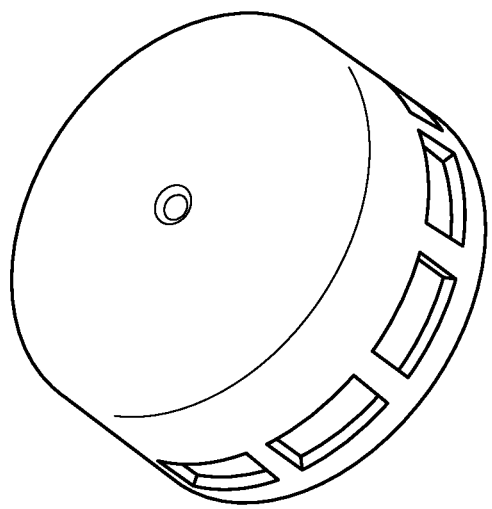
FIG. 24 is a perspective view of a heat moisture exchange filter according to an embodiment.
Figure 25:
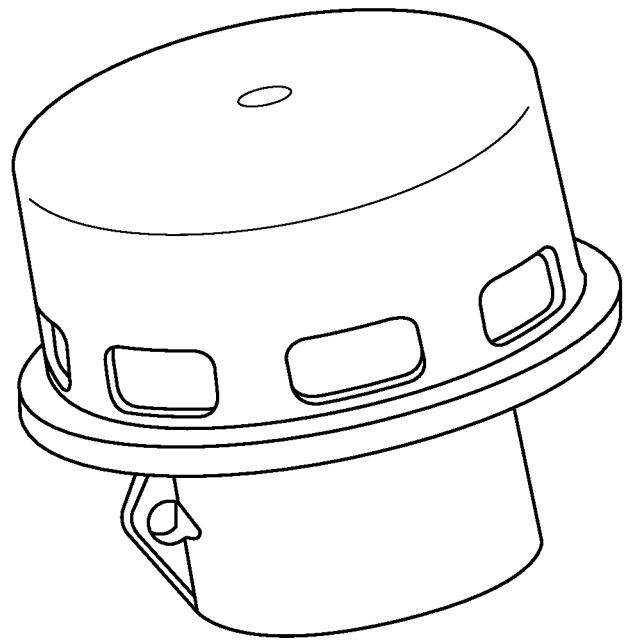
FIG. 25 is a perspective view of a heat moisture exchange filter connected to a speaking valve according to an embodiment.
Figure 26:
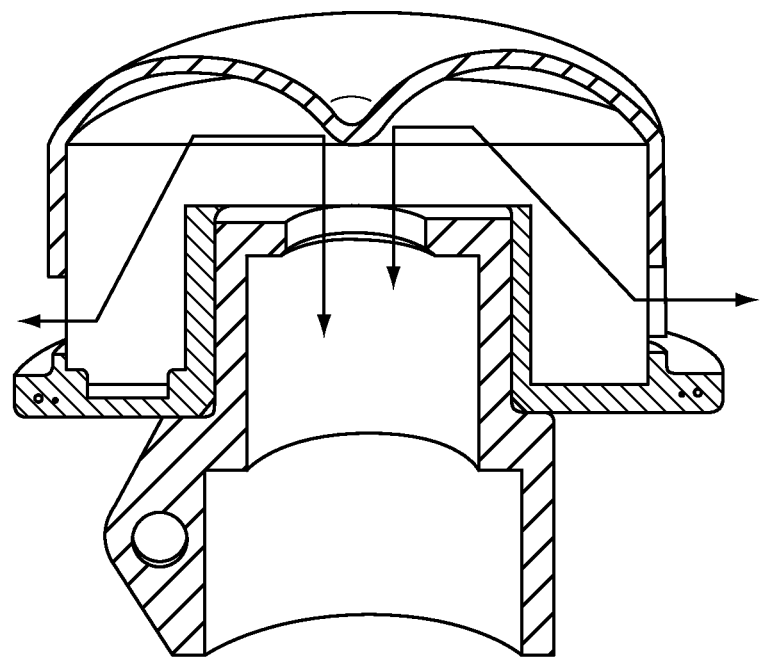
FIG. 26 is a cross-section view of the heat moisture exchange filter and speaking valve of FIG. 25.

FIGS. 23-25 are perspective views of an HME filter positioned on a speaking valve. FIG. 26 is a cross-section view of the HME filter of FIG. 23.

Figure 27:
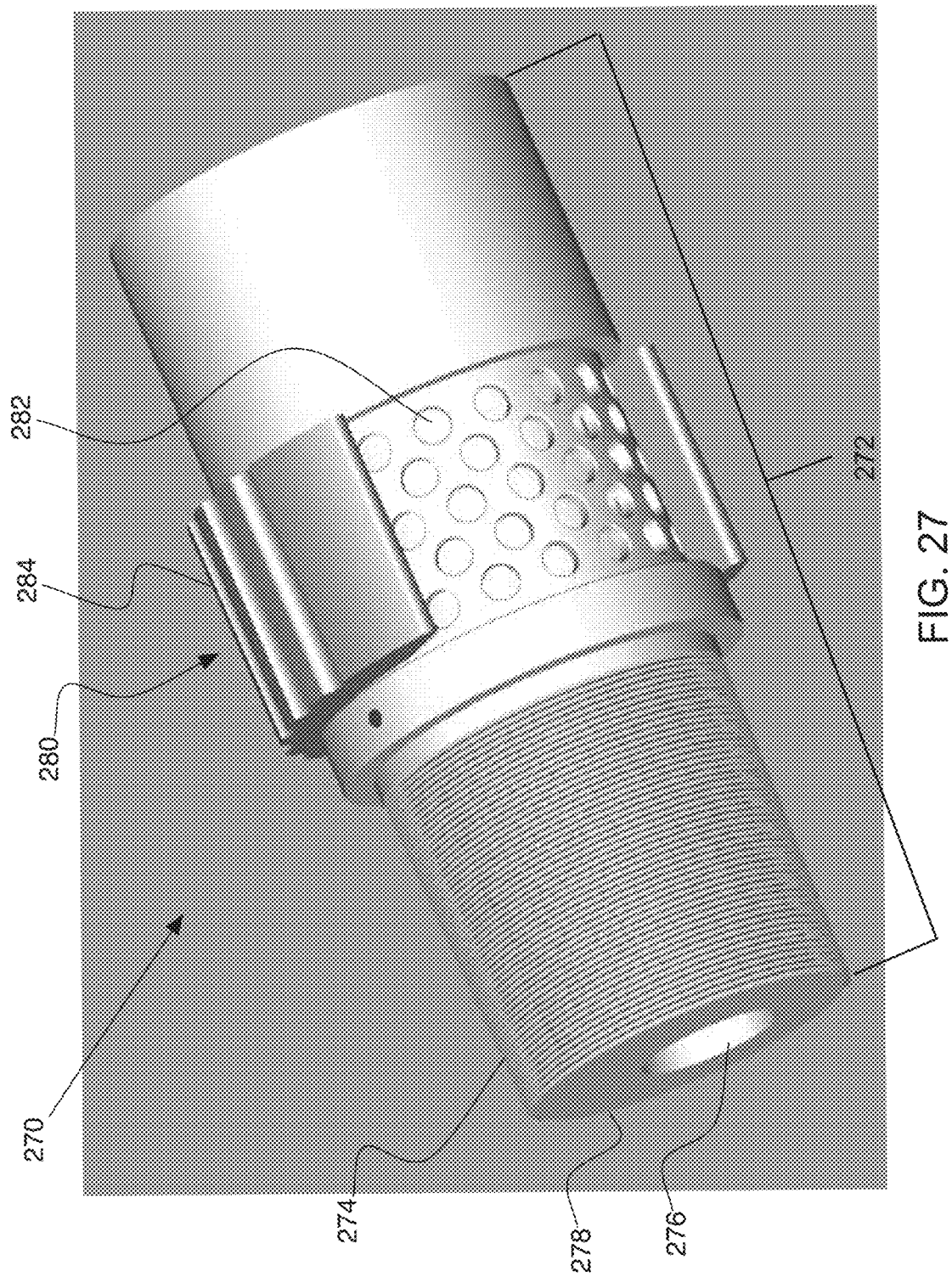
FIG. 27 is a perspective view of a speaking valve according to an embodiment.

FIG. 27 is a perspective view of a speaking valve 270 (Ventilator Speaking Valve) according to an embodiment which is similar in many respects to the non-ventilator valve (i.e., it consists of an external cylindrical housing chamber that contains a ball acting as the displaceable element). The ball moves back and forth during inspiration and expiration, and is limited proximally (tracheal side) from going beyond the housing chamber during inspiration by a ring and one or more circumferentially-spaced ramps disposed within the body of the chamber. Valve 270 has a frontal opening which is eccentric (off-center) and formed in the second end offset from a central axis of the chamber. This speaking valve has a unique protective feature which, in case of an erroneous inflation of the cuff by the staff, is designed to prevent closure of the airway circuit. The valve includes a series of fenestrations in the body, to allow variable and quantifiable degrees of air to escape. The fenestrations are able to be partially sealed in an adjustable and measured fashion, by a rotating ring that covers the holes. The degree of leak is adjustable by rotating a ring around the area of the fenestrations which occludes the fenestrations to a variable and quantifiable degree. This variable and adjustable feature allows the medical provider to gradually introduce the tracheotomized patient to the use of a ventilator speaking valve (hence minimizing patient reluctance toward cuff deflation, and making the initiation into a speaking valve more tolerable and less uncomfortable). Additionally and significantly, even in case of a human error and erroneous inflation of the tracheotomy cuff, the fenestrations in the body of the valve will act as effective relief ports and inflation of the tracheotomy cuff, the fenestrations in the body of the valve will act as effective relief ports and alleviate excessive trans-tracheal pressure, hence excluding the possibility of a completely closed air flow circuit, whilst still allowing enough airflow to the vocal cords to facilitate phonation.

Valve 270 comprises a cylindrical main body 272 having a chamber formed therein and having a stepped cylindrical frontal portion 274 attached. In at least some embodiments, main body 272 is formed in a single unit with frontal portion 274. A frontal opening 276 is formed in a front end 278 of frontal portion 274 and offset from the central axis of the valve 270. Frontal opening 276 is connectable to a ventilator. In at least some embodiments, frontal opening 276 is configured for connection to a ventilator. In at least some embodiments, frontal opening 276 is not configured to connect to a ventilator. In at least some embodiments, valve 270 is usable only connected with a ventilator. In at least some embodiments, valve 270 is usable not connected with a ventilator. Frontal portion 274 comprises a ridged outer portion for improving the ability of a user to grip valve 270 for manipulation. In at least some embodiments, the ridged outer portion is one of more bumps, indentations, or other suitable mechanism for improving grip. In at least some embodiments, frontal portion 274 does not include a ridged outer portion.

Main body 272 comprises a central portion 280 having openings 282 formed therein which extend between the interior chamber and the exterior of valve 270. A rotatable ring 284 is positioned exterior of main body 272 and at least partially overlaps a portion of openings 282. Rotatable ring 284 is rotatable about the perimeter of main body 272 to vary the number of openings 282 which are covered. Rotatable ring 284 surrounds at least a portion of the perimeter of main body 272. In at least some embodiments, rotatable ring 284 is a slidable cover configured to be slid to cover one or more of openings 282.

Figure 28:
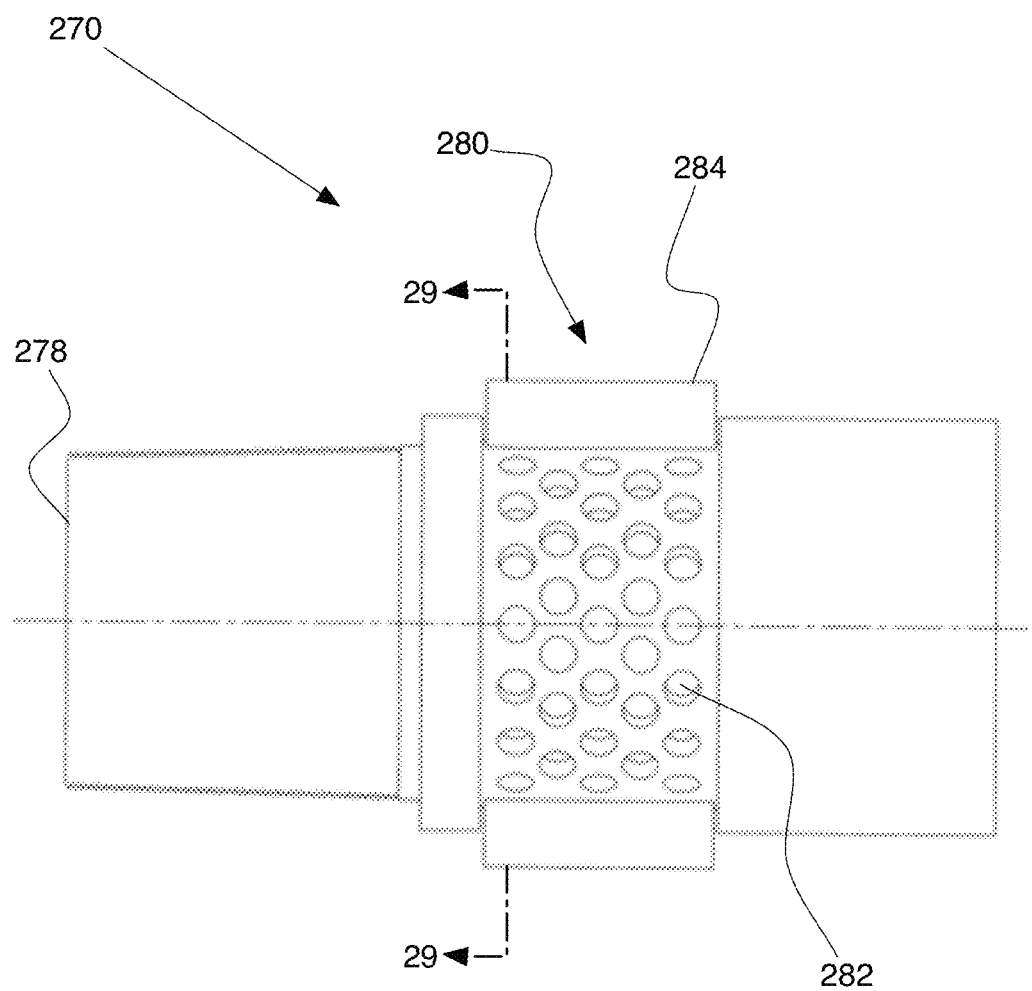
FIG. 28 is a side view of the speaking valve of FIG. 27.
Figure 29:
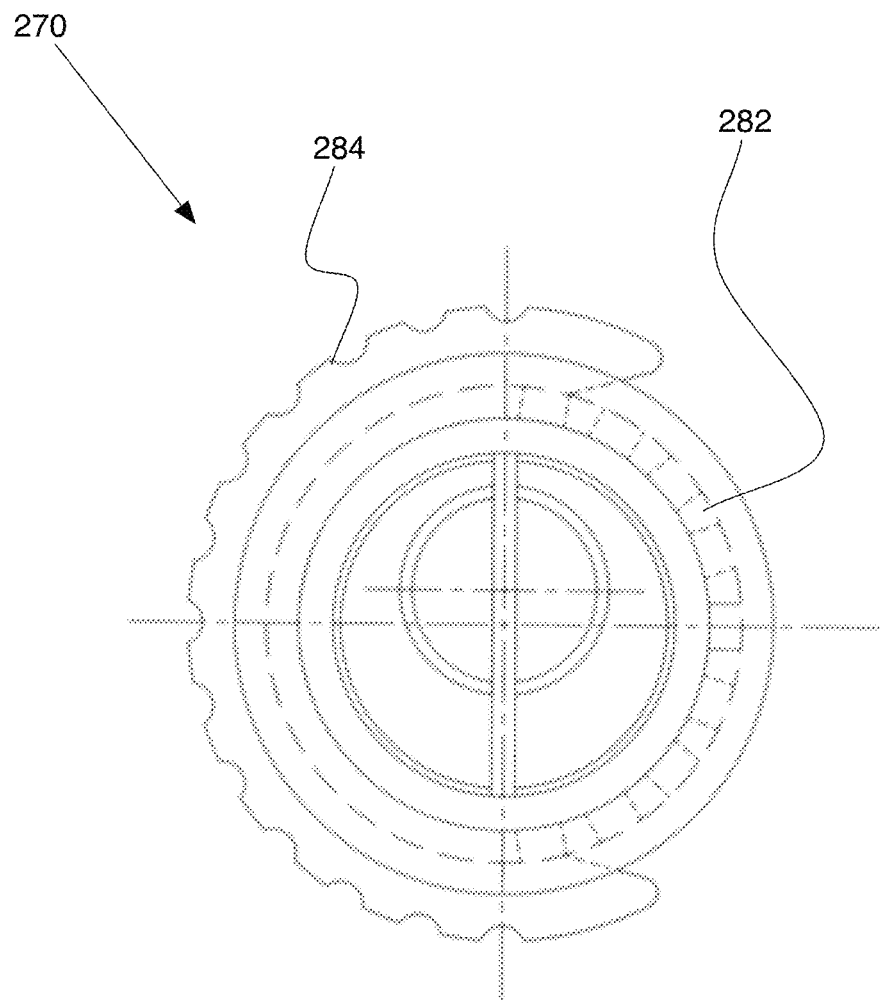
FIG. 29 is an axial cross-section view of the speaking valve of FIG. 27.
Figure 30:
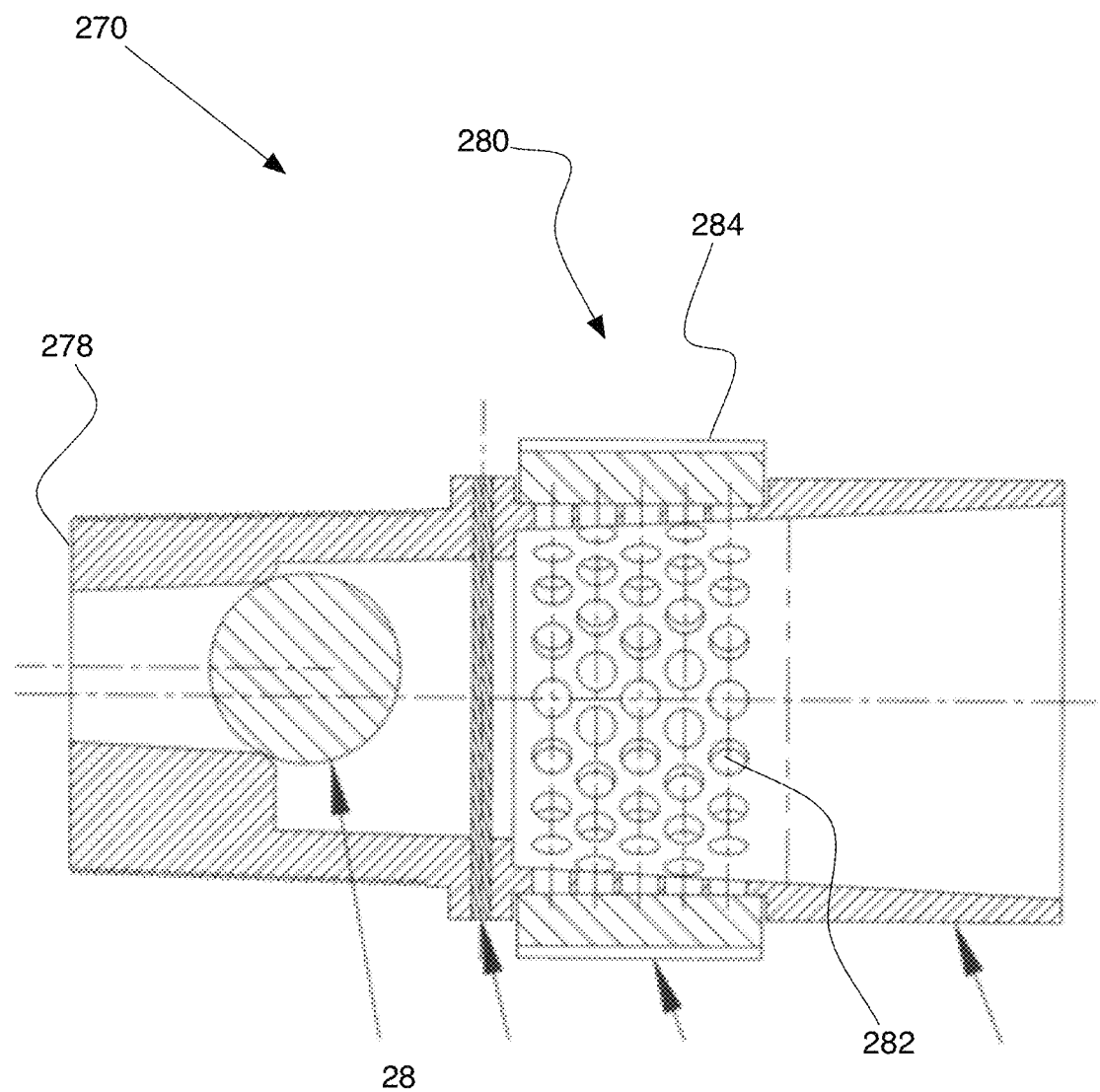
FIG. 30 is a longitudinal cross-section view of the speaking valve of FIG. 27.
Figure 31:
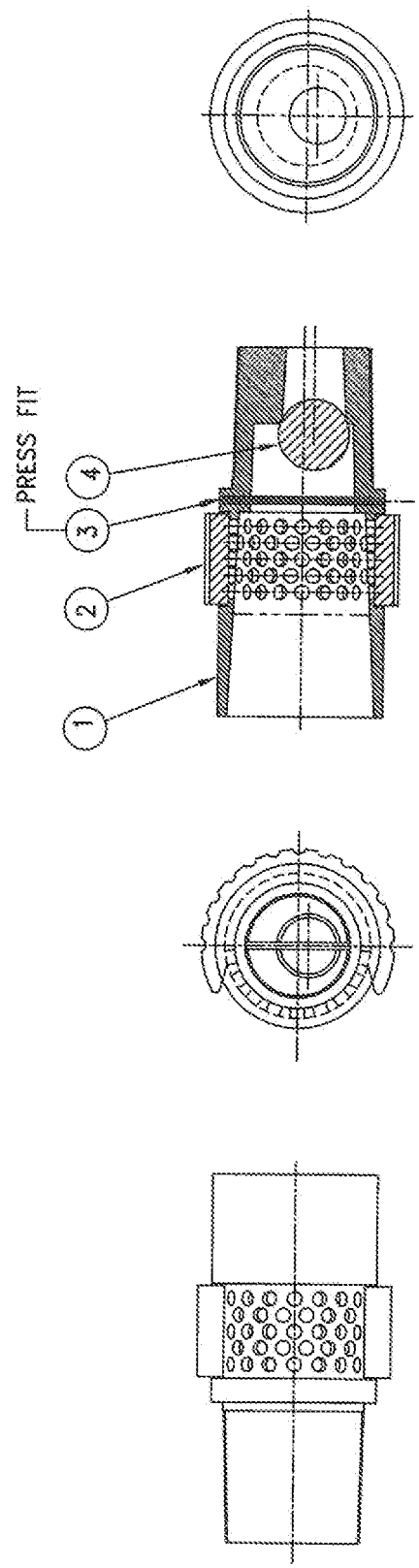
FIG. 31 is a plan, axial cross-section, longitudinal cross-section, and end view of the speaking valve of FIG. 27.
Figure 32:
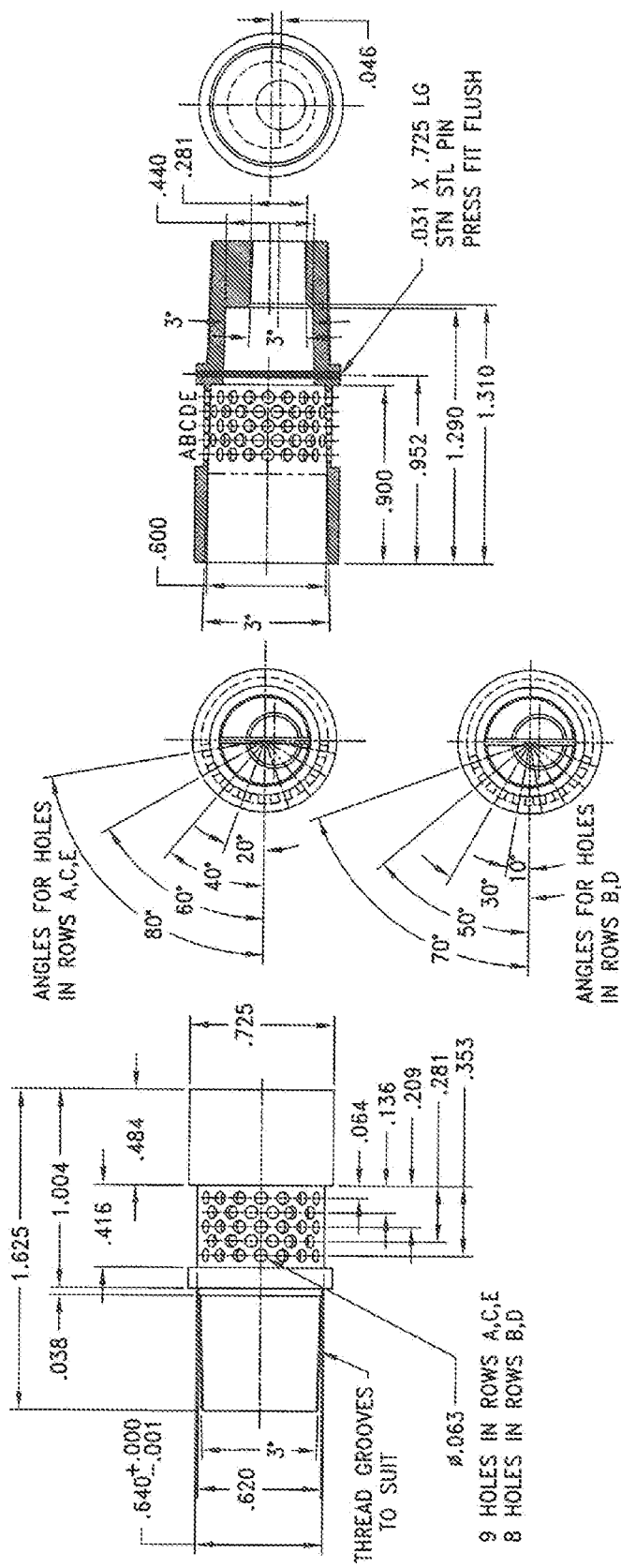
FIG. 32 is a plan, axial cross-section, longitudinal cross-section, and end view of the speaking valve of FIG. 27.
Figure 33:
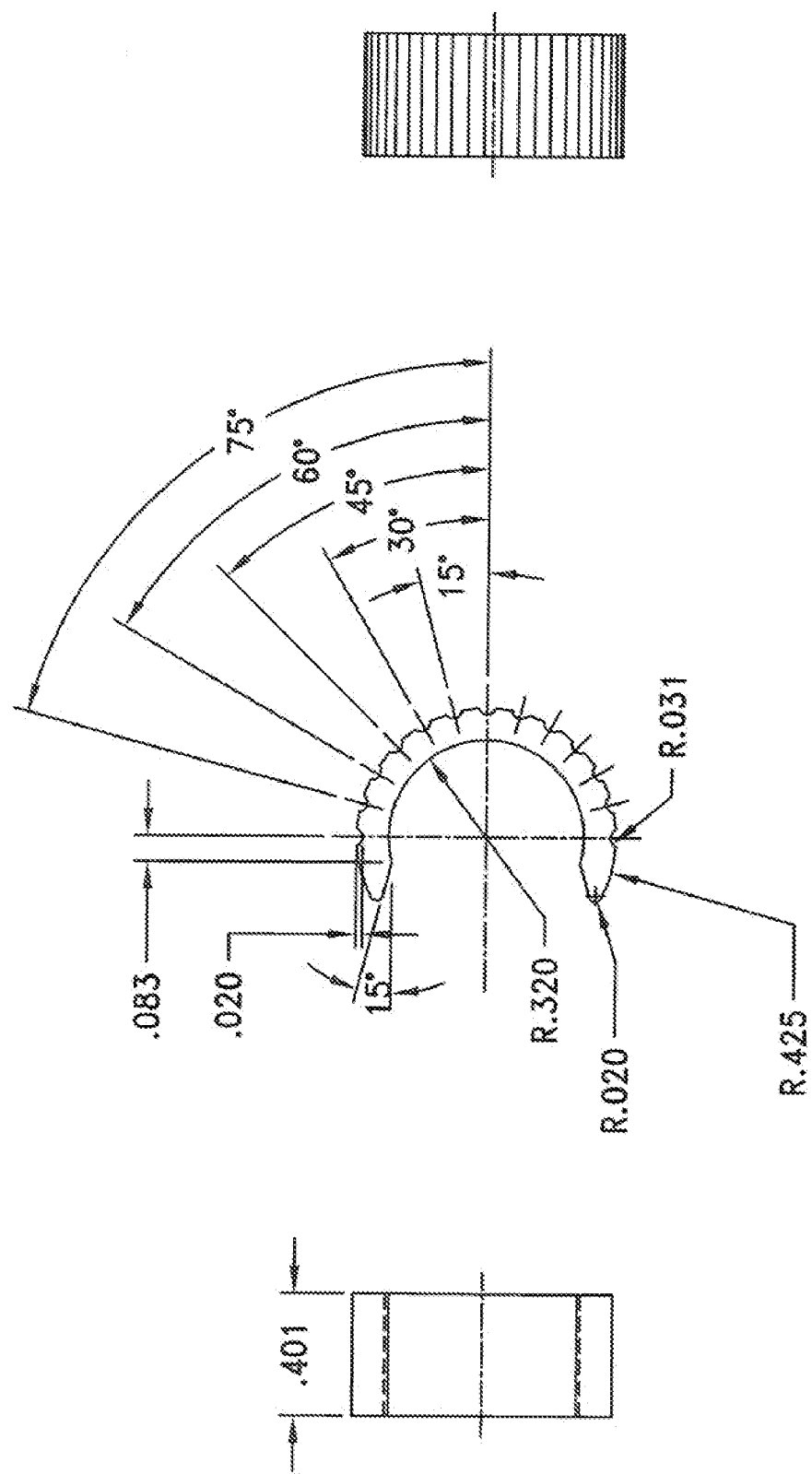
FIG. 33 is a side, axial cross-section, and opposite side view of a portion of the speaking valve of FIG. 27.

FIG. 28 is a side view of the FIG. 27 embodiment. FIG. 29 is a cross-section view of the FIG. 28 embodiment. FIG. 30 is a longitudinal cross-section view of the FIG. 28 embodiment.

It will be readily seen by one of ordinary skill in the art that the disclosed embodiments fulfill one or more of the advantages set forth above. After reading the foregoing specification, one of ordinary skill will be able to affect various changes, substitutions of equivalents and various other embodiments as broadly disclosed herein. It is therefore intended that the protection granted hereon be limited only by the definition contained in the appended claims and equivalents thereof.

What is claimed is:

1. A speaking valve for management of a patient's airway, the speaking valve comprising:
a body attachable to a tracheotomy tube at a first end, the body having a stepped chamber formed therein, the body having a second end distal from the first end, the first end having a frontal opening formed offset from a center of the first end, the body having at least one fenestration formed therein extending to connect the chamber to an exterior of the body;
a ball movable within the chamber and sized to close the frontal opening; and
a slidable cover coupled with the body, the slidable cover being C-shaped and positioned to selectably cover the at least one fenestration.

2. The speaking valve as claimed in claim 1, wherein the at least one fenestration is a plurality of fenestrations and wherein the slidable cover is sized to selectably cover at least a portion of the plurality of fenestrations.

3. The speaking valve as claimed in claim 2, wherein the slidable cover is configured to variably cover one or more of the plurality of fenestrations.

4. The speaking valve as claimed in claim 1, wherein the slidable cover is a rotatable ring coupled exterior of the body.

5. A method of managing a patient's airflow using a ventilator speaking valve, the speaking valve comprising a body attachable to a tracheotomy tube at a first end, the body having a stepped chamber formed therein, the body having a second end distal from the first end, the first end having a frontal opening formed offset from a center of the first end, the body having at least one fenestration formed therein extending to connect the chamber to an exterior of the body;
a ball movable within the chamber and sized to close the frontal opening; and
a slidable cover coupled with the body, the slidable cover being C-shaped and positioned to selectably cover the at least one fenestration, the method comprising:
positioning the slidable cover to cover the at least one fenestration.

6. The method as claimed in claim 5, wherein the at least one fenestration is more than one fenestration and the positioning the slidable cover
comprises positioning the slidable cover to cover all but one of the more than one fenestrations.

7. The method as claimed in claim 6, wherein with the frontal opening connected to a ventilator, the slidable cover positioned to cover all but one of the more than one fenestrations, air is able to flow out the remaining uncovered fenestration.

8. The method as claimed in claim 6, wherein with the ball in a position closing the frontal opening and the slidable cover positioned to cover all but one of the more than one fenestrations, air is able to flow out the remaining uncovered fenestration.

9. A speaking valve for management of a patient's airway, the speaking valve comprising:
a body attachable to a tracheotomy tube at a first end, the body having a stepped chamber formed therein, the body having a second end distal from the first end, the first end having a frontal opening formed offset from a center of the first end, the body having more than one fenestration formed therein extending to connect the chamber to an exterior of the body;
a ball movable within the chamber and sized to close the frontal opening; and
a slidable cover coupled with the body and positioned to selectably cover at least one of the more than one fenestration,
wherein the slidable cover only partially surrounds the body, has a first end separated from a second end by a gap such that the slidable cover is configured to cover each of the more than one fenestration, to expose each of the more than one fenestration, or to expose a selected quantity of the more than one fenestration.

10. The speaking valve as claimed in claim 9, wherein the slidable cover is a rotatable ring coupled exterior of the body.

11. A speaking valve for management of a patient's airway, the speaking valve comprising:
   a body attachable to a tracheotomy tube at a first end, the body having a stepped chamber formed therein, the body having a second end distal from the first end, the first end having a frontal opening formed offset from a center of the first end, the body having at least one fenestration formed therein extending to connect the chamber to an exterior of the body;
   a ball movable within the chamber and sized to close the frontal opening; and
   a slidable cover coupled with the body and positioned to selectably cover the at least one fenestration,
   wherein
      the slidable cover substantially surrounds the body,
      the slidable cover has a first end separated from a second end by a gap,
      the slidable cover is free from having an opening defined therein, and
      the body has a first side and a second side in a cross section view, the at least one fenestration is in the first side of the body, and the second side of the body is free from having a fenestration of the at least one fenestration.

12. The speaking valve as claimed in claim 11, wherein the at least one fenestration is a plurality of fenestrations and wherein the slidable cover is sized to selectably cover at least a portion of the plurality of fenestrations.

13. The speaking valve as claimed in claim 12, wherein the slidable cover is configured to variably cover one or more of the plurality of fenestrations.

14. The speaking valve as claimed in claim 11, wherein the slidable cover is a rotatable ring coupled exterior of the body.

15. A speaking valve for management of a patient's airway, the speaking valve comprising:
   a body attachable to a tracheotomy tube at a first end, the body having a stepped chamber formed therein, the body having a second end distal from the first end, the first end having a frontal opening formed offset from a center of the first end, the body having at least one fenestration formed therein extending to connect the chamber to an exterior of the body;
   a ball movable within the chamber and sized to close the frontal opening; and
   a slidable cover coupled with the body and positioned to selectably cover the at least one fenestration,
   wherein the slidable cover substantially surrounds the body, has a first end separated from a second end by a gap, and the slideable-slidable cover is free from having an opening defined therein.

16. The speaking valve as claimed in claim 15, wherein the at least one fenestration is a plurality of fenestrations and wherein the slidable cover is sized to selectably cover at least a portion of the plurality of fenestrations.

17. The speaking valve as claimed in claim 16, wherein the slidable cover is configured to variably cover one or more of the plurality of fenestrations.

18. The speaking valve as claimed in claim 15, wherein the slidable cover is a rotatable ring coupled exterior of the body.

19. A speaking valve for management of a patient's airway, the speaking valve comprising:
   a body attachable to a tracheotomy tube at a first end, the body having a stepped chamber formed therein, the body having a second end distal from the first end, the first end having a frontal opening formed offset from a center of the first end, the body having at least one fenestration formed therein extending to connect the chamber to an exterior of the body;
   a ball movable within the chamber and sized to close the frontal opening; and
   a slidable cover coupled with the body and positioned to selectably cover the at least one fenestration,
   wherein
      the slidable cover substantially surrounds the body,
      the slidable cover has a first end separated from a second end by a gap,
      the slidable cover is free from having an opening defined therein, and
      the body has a ridged surface on a sidewall between the first end and the at least one fenestration.

20. The speaking valve as claimed in claim 19, wherein the at least one fenestration is a plurality of fenestrations and wherein the slidable cover is sized to selectably cover at least a portion of the plurality of fenestrations.

21. The speaking valve as claimed in claim 20, wherein the slidable cover is configured to variably cover one or more of the plurality of fenestrations.

22. The speaking valve as claimed in claim 19, wherein the slidable cover is a rotatable ring coupled exterior of the body.

23. A speaking valve for management of a patient's airway, the speaking valve comprising:
   a body attachable to a tracheotomy tube at a first end, the body having a stepped chamber formed therein, the body having a second end distal from the first end, the first end having a frontal opening formed offset from a center of the first end, the body having at least one fenestration formed therein extending to connect the chamber to an exterior of the body;
   a ball movable within the chamber and sized to close the frontal opening; and
   a rotatable ring coupled with the body, the rotatable ring being a continuous structure surrounding at least half of a circumference of the body, and less than an entirety of the circumference of the body, the rotatable ring being configured to selectably cover all of the at least one fenestration, or to selectably cover a selected quantity of the at least one fenestration.

24. The speaking valve as claimed in claim 23, wherein the rotatable ring surrounds more than half of the circumference of the body.

25. The speaking valve as claimed in claim 1, wherein the body is cylindrical.

26. The speaking valve as claimed in claim 1, wherein the chamber is tapered such that an interior of the chamber is wider at a position corresponding to the at least one fenestration, and narrows in a direction extending from the at least one fenestration toward the frontal opening.

27. The speaking valve as claimed in claim 26, wherein the body has an exterior sidewall, and the exterior sidewall comprises a seat portion configured to accommodate the slidable cover.

28. The speaking valve as claims in claim 1, wherein the slidable cover has a ribbed surface on a side of the slidable cover.

* * * * *